United States Patent [19]

Costantini et al.

[11] Patent Number: 5,245,086
[45] Date of Patent: * Sep. 14, 1993

[54] HYDROXYLATION OF PHENOLS/PHENOL ETHERS

[75] Inventors: Michel Costantini; Dominique Laucher, both of Lyons, France

[73] Assignee: Rhone-Poulenc Chimie, Courbevoie, France

[*] Notice: The portion of the term of this patent subsequent to Mar. 17, 2009 has been disclaimed.

[21] Appl. No.: 622,635

[22] Filed: Dec. 5, 1990

[30] Foreign Application Priority Data

Dec. 5, 1989 [FR] France .................. 89 16312

[51] Int. Cl.$^5$ .................. C07C 41/26; C07C 37/60
[52] U.S. Cl. .................. 568/629; 568/716; 568/730; 568/747; 568/766; 568/768; 568/780; 568/784; 568/798; 568/771; 568/803; 568/763
[58] Field of Search .............. 568/730, 731, 744, 784, 568/715, 716, 764, 747, 629, 771, 780, 798, 766, 768, 803

[56] References Cited

U.S. PATENT DOCUMENTS

| | | | |
|---|---|---|---|
| 3,836,591 | 9/1974 | Maggioni | 260/671 G |
| 3,849,502 | 11/1974 | Bourdin et al. | 568/629 |
| 3,914,324 | 10/1975 | Maggioni | 260/621 G |
| 3,953,527 | 4/1976 | Bost et al. | 260/621 |
| 4,045,496 | 8/1977 | Seifert et al. | 260/613 D |
| 4,053,523 | 10/1977 | Seifert et al. | 260/621 |
| 4,078,006 | 3/1978 | Umemura et al. | 568/771 |
| 4,208,536 | 6/1980 | Costantini et al. | 568/771 |
| 4,223,165 | 9/1980 | Jouffret | 568/771 |
| 4,301,307 | 11/1981 | Jouffret | 568/771 |
| 5,097,078 | 3/1992 | Costantini et al. | 568/803 |

FOREIGN PATENT DOCUMENTS

| | | |
|---|---|---|
| 2064497 | 7/1971 | Fed. Rep. of Germany. |
| 2138735 | 3/1973 | Fed. Rep. of Germany. |
| 075041 | 2/1974 | Japan .................. 568/771 |

Primary Examiner—Marianne M. Cintins
Assistant Examiner—Margaret J. Page
Attorney, Agent, or Firm—Burns, Doane, Swecker & Mathis

[57] ABSTRACT

The phenols/phenol ethers are hydroxylated by reaction with hydrogen peroxide, in the presence of a catalytically effective amount of (a) at least one alkali metal or alkaline earth metal salt of a protonic acid having a pKa in water of less than −0.1 and (b) a free protonic acid.

24 Claims, No Drawings

HYDROXYLATION OF PHENOLS/PHENOL ETHERS

BACKGROUND OF THE INVENTION

1. Field of the Invention

The present invention relates to the hydroxylation of phenols and ethers of phenols with hydrogen peroxide, and, more especially, to the hydroxylation of such phenols/phenol ethers with $H_2O_2$ in the presence of a catalytically effective amount of at least one alkali or alkaline earth metal salt of a protonic acid, as well as a free protonic acid.

2. Description of the Prior Art

French Patent No. 69/45,467, published under Number 2,071,464, describes a process for hydroxylating phenols and ethers of phenols with hydrogen peroxide in the presence of a strong acid. The most typically used strong acids are sulfuric, para-toluene sulfonic and perchloric.

The process described in the '467 patent is a very important industrial process. However, serious need continues to exist for a catalyst for that reaction which would be less corrosive to the apparatus employed and would provide at least as good yields, as has been reported in the literature.

Thus, published French Patent Application FR 2,489,816 recommends using the silicalites of various metals for such purpose.

And European Patent Application EP-A-0,299,893 offers the use of bridged clays.

Although these methods employing heterogeneous catalysis appear interesting, they do not address such industrial problems as the recycling of the catalyst, its regeneration and the aging thereof.

SUMMARY OF THE INVENTION

Accordingly, a major object of the present invention is the provision of an improved process for the hydroxylation of phenols/phenol ethers, which improved process provides higher yields than those that can be attained using catalytically effective amounts of the strong acids.

Briefly, the present invention features a process for hydroxylating phenols or ethers of phenols, having the general formula (I):

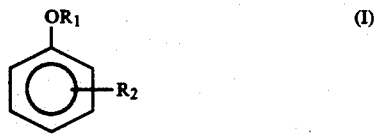

wherein $R_1$ is a hydrogen atom, a methyl radical, an ethyl radical or a phenyl radical, and $R_2$ is a hydrogen atom, an alkyl radical having from 1 to 4 carbon atoms, an alkoxy radical having from 1 to 4 carbon atoms or a phenyl or cyclohexyl radical, comprising reacting such phenol/phenol ether with hydrogen peroxide, in the presence of a catalytically effective amount of (a) at least one alkali metal or alkaline earth metal salt of a protonic acid having a pKa, in water, of less than $-0.1$ and (b) a free protonic acid.

DETAILED DESCRIPTION OF THE PREFERRED EMBODIMENTS OF THE INVENTION

More particularly according to the present invention, the protonic acids which serve as catalysts are preferably those having a pKa in water of less than $-1$.

By "pKa" is intended the ionic dissociation constant of the acid/base pair when water is used as the solvent.

Of the acids within this definition, it is preferable to use those which are stable vis-a-vis oxidation by hydrogen peroxide.

The following acids are particularly representative: sulfuric, pyrosulfuric, perchloric, nitric, halosulfonic acids such as fluorosulfonic, chlorosulfonic or trifluoromethane sulfonic, methane sulfonic acid, ethane sulfonic acid, ethane disulfonic acid, benzene sulfonic acid, or the benzene disulfonic, toluene sulfonic, naphthalene sulfonic or naphthalene disulfonic acids.

Preferred such acids are sulfuric, perchloric, trifluoromethane sulfonic, para-toluene sulfonic, chlorosulfonic, fluorosulfonic or methane sulfonic.

The alkali metal or alkaline earth metal salts of the protonic acid defined above, which are used together with a free protonic acid, are advantageously alkali metal or alkaline earth metal salts of sulfuric, pyrosulfuric, perchloric or nitric acid, of halosulfonic acids such as chlorosulfonic, fluorosulfonic or trifluoromethane sulfonic, of methane sulfonic, ethane sulfonic, ethane disulfonic or benzene sulfonic acid, or of benzene disulfonic, toluene sulfonic, naphthalene sulfonic or naphthalene disulfonic acids.

By "alkali metal salts" are intended the neutral salts of such acids of lithium, sodium, potassium, rubidium and cesium.

The sodium or potassium salts are typically the preferred; for economic reasons it is more preferred to use the sodium salts.

Exemplary such preferred salts include disodium sulfate, sodium perchlorate, sodium trifluoromethane sulfonate, sodium para-toluene sulfonate, sodium chlorosulfonate, sodium fluorosulfonate and sodium methane sulfonate.

By "alkaline earth metal salts" are intended the neutral salts of such acids of beryllium, magnesium, calcium, strontium and barium.

The magnesium, calcium and barium salts are typically the preferred.

Preferred such alkaline earth metal salts are calcium sulfate, magnesium sulfate, calcium perchlorate, magnesium perchlorate, calcium trifluoromethane sulfonate, magnesium trifluoromethane sulfonate, calcium para-toluene sulfonate, magnesium para-toluene sulfonate, calcium fluorosulfonate, magnesium fluorosulfonate, calcium methane sulfonate and magnesium methane sulfonate.

Mixtures of a plurality of alkali metal or alkaline earth metal salts of the same protonic acid may also be used.

The total amount of protonic acid and alkali metal or alkaline earth metal salt may vary widely.

It is typically expressed as the molar ratio of the protonic acid plus the alkali metal or alkaline earth metal salt to the hydrogen peroxide.

This ratio advantageously ranges from 0.1 to 25 molar percent and preferably from 0.5 to 15 molar percent.

The molar ratio of the alkali metal or alkaline earth metal salt to the free protonic acid advantageously ranges from 0.2 to 20:1 and preferably from 0.5 to 10:1.

The alkali metal or alkaline earth metal salt may be prepared in situ, for example by mixing the protonic acid to be used with an alkali metal or alkaline earth metal oxide or hydroxide, in amounts such that there exists a stoichiometric excess of the acid.

The excess is calculated such that the molar ratio of the alkali metal or alkaline earth metal salt to the free protonic acid is within the range of values indicated above.

An oxacid of phosphorus may advantageously be used together with the catalyst comprising the protonic acids and the alkali metal or alkaline earth metal salts thereof, to improve the yield of diphenols.

The oxacids of phosphorus are advantageously acid function compounds of phosphorus, the phosphorus being in an oxidation state of 5.

Acid function compounds of phosphorus in the oxidation state of 3 may also be used. These will be oxidized in the reaction medium by the hydrogen peroxide to corresponding compounds of phosphorus (V). But this embodiment is of no particular commercial interest, and presents the drawback of consuming a portion of the hydrogen peroxide.

Such oxacids of phosphorus (V) include orthophosphoric, metaphosphoric, pyrophosphoric acid, polyphosphoric acids and phosphonic acids, such as (1-hydroxy ethylidene)diphosphonic, phosphonic, ethyl phosphonic or phenyl phosphonic acid.

The amount of phosphorus oxacid, expressed as a molar ratio of phosphorus oxacid to hydrogen peroxide, advantageously ranges from 0.5% to 20% and preferably from 0.1% to 10%.

The hydrogen peroxide may be used in the form of an aqueous solution, or an organic solution.

Aqueous solutions are preferred since they are commercially available. They typically contain over 20% by weight of hydrogen peroxide.

The amount of hydrogen peroxide is advantageously up to 1 mol of $H_2O_2$ per mol of the phenolic compound of formula (I).

If industrially acceptable yields are to be attained, however, it is preferred to use a molar ratio of phenolic compound of formula (I) to hydrogen peroxide ranging from 25:1 to 3:1 and preferably from 20:1 to 4:1.

Exemplary phenolic compounds of formula (I) include phenol, anisole, orthocresol, para-cresol, metacresol, 4-tert-butyl phenol, 2-methoxy phenol or 4-methoxy phenol.

The invention is more particularly suitable for preparing hydroquinone and pyrocatechol from phenol.

The hydroxylation process is typically carried out without any solvent other than that emanating from the reagents, such as the solvent of the hydrogen peroxide.

However, the reaction may be carried out equally as well in a solvent for the phenolic compound (I).

There are many solvents which may be used, if appropriate.

Exemplary thereof are the non-polar solvents, such as chlorinated aliphatic hydrocarbons, e.g., dichloromethane, tetrachloromethane or dichloroethane.

Also exemplary thereof are the essentially nonpolar solvents, such as alcohols and ethers, e.g., methanol, tertiobutanol, isopropanol, ethanol or methyl tertiobutyl ether, as are the highly polar solvents, such as water.

In general, the non-polar solvents are more favorable and are the preferred.

The temperature at which the hydroxylation reaction is carried out advantageously ranges from 45° to 160° C. at atmospheric pressure.

It is also possible to conduct the reaction at higher temperatures at a pressure above atmospheric.

The reagents and operating conditions are well suited for continuously carrying out the process of the invention.

In order to further illustrate the present invention and the advantages thereof, the following specific examples are given, it being understood that same are intended only as illustrative and in nowise limitative.

EXAMPLES 1 TO 6 AND COMPARATIVE EXAMPLES A, B AND C

The following reagents were introduced into a 100 cm³ glass flask fitted with a reflux condenser, a thermometer, a pouring funnel and a central agitator:
  (i) phenol: 47 g (0.5 mol);
  (ii) perchlorate: nature and molar ratio to $H_2O_2$ indicated in Table I;
  (iii) perchloric acid: molar ratio to $H_2O_2$ indicated in Table I;
  (iv) pyrophosphoric acid: molar ratio to $H_2O_2$ indicated in Table I.

When the mixture had been brought to 75° C. with agitation, an aqueous solution of hydrogen peroxide was introduced, in an amount such that there was established a molar ratio of $H_2O_2$ to phenol of 10% or 5%.

After being heated to 75° C. for the periods of time indicated in Table I, the sample was cooled, any remaining hydrogen peroxide was analyzed by iodometry, and the diphenols formed were analyzed by high performance liquid chromatography (HPLC).

The results obtained are reported in Table I below.

The following abbreviations are used in the Table I:
CR %: degree of conversion of $H_2O_2$ as a percentage
Y % HQ: percent yield of hydroquinone relative to $H_2O_2$ converted
Y % PC: percent yield of pyrocatechol relative to $H_2O_2$ converted
Y % total: total percent yield of diphenols relative to $H_2O_2$ converted.

It will be appreciated that the total yield of diphenols was higher when the hydroxylation reaction was catalyzed by perchloric acid and a metal perchlorate than when the catalysis was effected solely by means of perchloric acid.

If Example 1 is compared with Comparative Example A (for the same $ClO_4^-/H_2O_2$ ratio), it will be seen that the yield was higher with the perchloric acid/magnesium perchlorate mixture than with perchloric acid alone.

TABLE I

| EXAMPLE | $H_2O_2$/phenol (mole %) | $HClO_4/H_2O_2$ (mole %) | Salt Nature | Salt/$H_2O_2$ (mole %) | $H_4P_2O_7$/$H_2O_2$ (mole %) | Duration of test | CR % $H_2O_2$ | Y % HQ | Y % PC | Y % total | PC/HQ |
|---|---|---|---|---|---|---|---|---|---|---|---|
| Example 1 | 10 | 1.2 | Mg(ClO$_4$)$_2$ | 3.6 | 0.6 | 1 h | 99.5 | 32.0 | 45.0 | 77.0 | 1.4 |

TABLE I-continued

| EXAMPLE | $H_2O_2$/phenol (mole %) | $HClO_4/H_2O_2$ (mole %) | Salt Nature | Salt/$H_2O_2$ (mole %) | $H_4P_2O_7$/ $H_2O_2$ (mole %) | Duration of test | CR % $H_2O_2$ | Y % HQ | Y % PC | Y % total | PC/HQ |
|---|---|---|---|---|---|---|---|---|---|---|---|
| Comparative Example A | 10 | 8.4 | none | 0 | 0.6 | 0 h, 50 min | 100 | 13.0 | 31.5 | 44.5 | 2.4 |
| Example 2 | 10 | 1.2 | Mg(ClO$_4$)$_2$ | 7.9 | 0.6 | 2 h, 25 min | 100 | 31.5 | 44.0 | 75.5 | 1.4 |
| Example 3 | 10 | 1.3 | NaClO$_4$.H$_2$O | 3.6 | 0.6 | 2 h, 30 min | 99.5 | 28.5 | 45.0 | 73.5 | 1.6 |
| Example 4 | 10 | 1.3 | NaClO$_4$.H$_2$O | 7.3 | 0.6 | 1 h | 99 | 29.5 | 44.0 | 73.5 | 1.5 |
| Comparative Example B | 10 | 1.3 | none | 0 | 0.6 | 2 h, 25 min | 100 | 30.0 | 42.0 | 72.0 | 1.4 |
| Example 5 | 5 | 1.4 | Mg(ClO$_4$)$_2$ | 1.2 | 0.6 | 0 h, 40 min | 100 | 37.0 | 51.0 | 88.0 | 1.4 |
| Example 6 | 5 | 2.3 | Mg(ClO$_4$)$_2$ | 14 | 1.3 | 0 h, 30 min | 100 | 38.0 | 49.5 | 87.5 | 1.3 |
| Comparative Example C | 5 | 1.4 | none | 0 | 0.6 | 1 h | 100 | 35.0 | 49.0 | 84.0 | 1.4 |

EXAMPLES 7 TO 14 AND COMPARATIVE EXAMPLES D AND E

The procedure of Examples 1 to 6 was repeated, using sulfuric acid and a sodium or magnesium sulfate as catalysts.

All of the tests were carried out using 0.6 molar percent of $H_4P_2O_7$ relative to $H_2O_2$.

Table II below indicates the nature of the various catalysts, the amount thereof (as a molar percentage relative to $H_2O_2$), the amount of $H_2O_2$ (as a molar percentage relative to phenol), the temperature, the duration of the test and the results obtained.

The abbreviations used are the same as for Table I.

EXAMPLES 15 TO 18 AND COMPARATIVE EXAMPLES F, G AND H

Tests in a Solvent Medium

The procedure of Examples 1 to 6 was repeated, operating in the presence of a solvent, which was either dichloromethane or water.

The tests were carried out using 0.3 molar percent of $H_4P_2O_7/H_2O_2$.

Table III below indicates the nature of the catalysts, the amount thereof (as a molar percentage relative to $H_2O_2$), the amount of $H_2O_2$ (as a molar percentage relative to phenol), the amount of solvent, the temperature, the duration of the test and the results obtained.

TABLE II

| EXAMPLE | $H_2O_2$/phenol (mole %) | $H_2SO_4/H_2O_2$ (mole %) | Salt Nature | Salt/$H_2O_2$ (mole %) | Temperature °C. | Duration of test | CR % $H_2O_2$ | Y % HQ | Y % PC | Y % total | PC/HQ |
|---|---|---|---|---|---|---|---|---|---|---|---|
| Example 7 | 5.5 | 1.1 | Na$_2$SO$_4$.H$_2$O | 2.7 | 75 | 6 h, 40 min | 96.5 | 27.0 | 54.5 | 81.5 | 2.0 |
| Example 8 | 5 | 1.7 | Na$_2$SO$_4$.H$_2$O | 3.7 | 75 | 1 h, 45 min | 100 | 28.5 | 55.5 | 84.0 | 1.95 |
| Example 9 | 6 | 1.5 | Na$_2$SO$_4$.H$_2$O | 5.2 | 75 | 4 h, 30 min | 100 | 28.5 | 57.0 | 85.5 | 2.0 |
| Example 10 | 5 | 1.5 | MgSO$_4$.7H$_2$O | 3.7 | 100 | 1 h | 100 | 28.5 | 56.0 | 84.5 | 1.95 |
| Example 11 | 5 | 2.0 | MgSO$_4$ | 3.0 | 100 | 1 h | 100 | 29.0 | 55.5 | 84.5 | 2.0 |
| Example 12 | 5 | 1.2 | MgSO$_4$ | 3.6 | 100 | 1 h | 100 | 28.5 | 57.0 | 85.5 | 2.0 |
| Example 13 | 5 | 1.8 | MgSO$_4$ | 4.2 | 100 | 1 h | 100 | 28.5 | 56.0 | 84.5 | 2.0 |
| Example 14 | 10 | 1.4 | MgSO$_4$ | 3.7 | 100 | 1 h | 100 | 25.5 | 50.0 | 75.5 | 1.95 |
| Comparative Example D | 5 | 1.4 | none | 0 | 75 | 4 h, 30 min | 100 | 27.0 | 53.0 | 80.0 | 1.95 |
| Comparative Example E | 5.5 | 1.4 | none | 0 | 100 | 1 h | 100 | 27.0 | 52.5 | 79.5 | 1.95 |

TABLE III

| EXAMPLE | $H_2O_2$/phenol (mole %) | Acid/$H_2O_2$ (mole %) | Salt Nature | Salt/$H_2O_2$ (mole %) | Solvent weight | Temperature °C. | Duration of test | CR % $H_2O_2$ | Y % HQ | Y % PC | Y % total | PC/HQ |
|---|---|---|---|---|---|---|---|---|---|---|---|---|
| Example 15 | 5.5 | H$_2$SO$_4$ 1.5 | MgSO$_4$ | 3.2 | CH$_2$Cl$_2$ 12.8 g | 75 | 3 h, 30 min | 100 | 24.5 | 56.5 | 81.0 | 2.3 |
| Comparative Example F | 5.5 | H$_2$SO$_4$ 1.7 | none | 0 | CH$_2$Cl$_2$ 12.8 g | 75 | 3 h, 30 min | 100 | 22.0 | 53.0 | 75.0 | 2.4 |
| Example 16 | 5.5 | H$_2$SO$_4$ 1.5 | MgSO$_4$ | 3.3 | H$_2$O 2.7 g | 100 | 3 h, 10 min | 100 | 23.0 | 47.0 | 70.0 | 2.0 |
| Example 17 | 5.5 | H$_2$SO$_4$ 1.5 | MgSO$_4$ | 10.1 | H$_2$O 2.7 g | 100 | 3 h | 100 | 22.5 | 48.5 | 71.0 | 2.2 |
| Comparative Example G | 5.5 | H$_2$SO$_4$ 1.9 | none | 0 | H$_2$O 2.7 g | 100 | 1 h, 30 min | 99.5 | 10.0 | 33.5 | 43.5 | 3.3 |
| Example 18 | 5.0 | HClO$_5$ 1.3 | Mg(ClO$_4$)$_2$ | 3.6 | CH$_2$Cl$_2$ 12.8 g | 75 | 2 h | 100 | 33.5 | 49.5 | 83.0 | 1.5 |
| Comparative Example H | 5.5 | HClO$_4$ 1.3 | none | 0 | CH$_2$Cl$_2$ 12.8 g | 75 | 2 h, 10 min | 100 | 32.0 | 48.5 | 80.5 | 1.5 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for hydroxylating a phenol or phenol ether having the formula (I):

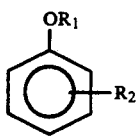

wherein $R_1$ is a hydrogen atom, a methyl radical, an ethyl alkyl radical having from 1 to 4 carbon atoms, an alkoxy radical having from 1 to 4 carbon atoms or a phenyl or cyclohexyl radical, comprising reacting such phenol or phenol ether with hydrogen peroxide, in the presence of a catalytically effective amount of (a) at least one alkali metal or alkaline earth metal salt of a protonic acid having a pKa, in water, of less than $-0.1$ and (b) a free protonic acid.

2. The process as defined by claim 1, said protonic acids having a pKa in water of less than $-1$.

3. The process as defined by claim 1, wherein said protonic acids are sulfuric acid, pyrosulfuric acid, perchloric acid, nitric acid, a halosulfonic acid, methane sulfonic acid, ethane sulfonic acid, ethane disulfonic acid, benzene sulfonic acid, a benzene disulfonic acid, a toluene sulfonic acid, a naphthalene sulfonic acid, or a naphthalene disulfonic acid.

4. The process as defined by claim 3, wherein said process is carried out in the presence of a lithium, sodium, potassium, rubidium or cesium salt of said protonic acids.

5. The process as defined by claim 4, wherein said process is carried out in the presence of disodium sulfate, sodium perchlorate, sodium trifluoromethane sulfonate, sodium para-toluene sulfonate, sodium chlorosulfonate, sodium fluorosulfonate or sodium methane sulfonate.

6. The process as defined by claim 3, wherein said process is carried out in the presence of a beryllium, magnesium, calcium, strontium or barium salt of said protonic acids.

7. The process as defined by claim 6, wherein said process is carried out in the presence of calcium sulfate, magnesium sulfate, calcium perchlorate, magnesium perchlorate, calcium trifluoromethane sulfonate, magnesium trifluoromethane sulfonate, calcium para-toluene sulfonate, magnesium para-toluene sulfonate, calcium fluorosulfonate, magnesium fluorosulfonate, calcium methane sulfonate or magnesium methane sulfonate.

8. The process as defined by claim 1, wherein said process is carried out in the presence of an oxacid of phosphorus.

9. The process as defined by claim 8, said oxacid of phosphorus comprising a phosphorus (V) acid.

10. The process as defined by claim 9, said oxacid of phosphorus (V) comprising orthophosphoric acid, metaphosphoric acid, or a phosphonic acid.

11. The process as defined by claim 9, said oxacid of phosphorus (V) comprising orthophosphoric, pyrophosphoric or (1-hydroxyethylidene)disphosphonic acid.

12. The process as defined by claim 1, wherein the total amount of protonic acid and alkali metal or alkaline earth metal salt, expressed as a molar ratio of protonic acid plus alkali metal or alkaline earth metal salt, to hydrogen peroxide, ranges from 0.1% to 25%.

13. The process as defined by claim 1, wherein the molar ratio of alkali metal or alkaline earth metal salt to protonic acid ranges from 0.2 to 20:1.

14. The process as defined by claim 8, wherein the amount of phosphorus oxacid, expressed as a molar ratio of phosphorus oxacid to hydrogen peroxide, ranges from 0.05% to 20%.

15. The process as defined by claim 1, wherein the molar ratio of the phenolic compound of formula (I) to hydrogen peroxide ranges from 25:1 to 3:1.

16. The process as defined by claim 1, said phenolic compound of formula (I) comprising phenol, anisole, ortho-cresol, para-cresol, meta-cresol, 4-tert-butylphenol, 2-methoxyphenol or 4-methoxyphenol.

17. The process as defined by claim 1, carried out at a temperature ranging from 45° to 160° C. and at about atmospheric pressure.

18. The process as defined by claim 1, carried out in a chlorinated aliphatic hydrocarbon solvent.

19. The process as defined by claim 12, said total amount ranging from 0.5% to 15%.

20. The process as defined by claim 13, said molar ratio ranging from 0.5 to 10:1.

21. The process as defined by claim 14, said amount of phosphorus oxacid ranging from 0.1% to 10%.

22. The process as defined by claim 15, said molar ratio ranging from 20:1 to 4:1.

23. The process as defined in claim 9, wherein said oxacid of phosphorus (V) comprises pyrophosphoric acid.

24. The process as defined in claim 9, wherein said oxacid phosphorus (V) comprises a polyphosphoric acid.

* * * * *